United States Patent [19]
Coles et al.

[11] 4,253,828
[45] Mar. 3, 1981

[54] ORTHODONTIC APPLIANCE

[76] Inventors: Donna C. Coles, c/o Dens Company, 174 W. Live Oak, Arcadia, Calif. 91006; Jerry P. Honstein, 6543 W. Circulo Dali, Anaheim Hills, Calif. 92807

[21] Appl. No.: 28,112

[22] Filed: Apr. 9, 1979

[51] Int. Cl.³ .............................................. A61C 7/00
[52] U.S. Cl. .................................................... 433/6
[58] Field of Search ........................................ 433/6, 7

[56] References Cited
U.S. PATENT DOCUMENTS

| 646,629 | 4/1908 | Sugatt | 433/6 |
|---|---|---|---|
| 2,467,432 | 4/1949 | Kesling | 433/6 |
| 2,479,780 | 8/1949 | Remensnyder | 433/6 |
| 2,789,351 | 4/1957 | Gordon | 433/6 |
| 3,849,885 | 11/1974 | Robins | 433/6 |
| 4,073,061 | 2/1978 | Bergersen | 433/6 |
| 4,139,944 | 2/1979 | Bergersen | 433/6 |

Primary Examiner—Robert Peshock
Attorney, Agent, or Firm—Gausewitz, Carr, Rothenberg & Edwards

[57] ABSTRACT

This invention provides an orthodontic appliance of generally U-shaped configuration conforming to the natural arch of the patient, having a flexible outer portion adapted to overlie portions of the facial surfaces on the teeth of a row of teeth, an inner portion of greater rigidity than the outer portion for engaging portions of the lingual surfaces of a row of teeth and overlying the gingiva, and interconnecting portions at the ends of the appliance that fit around the posterior teeth of a row of teeth, with the crowns of the teeth extending upwardly through the opening and unobstructed by the appliance. The surfaces of the inner and outer portions are made to accomplish various tooth movements or tooth retention as desired by appropriately engaging the surfaces of the teeth. Greater degrees of movement may be accomplished by splitting the inner and outer portions and providing resilient members that urge the split segments of the outer portion together and the split segments of the inner portion apart.

27 Claims, 20 Drawing Figures

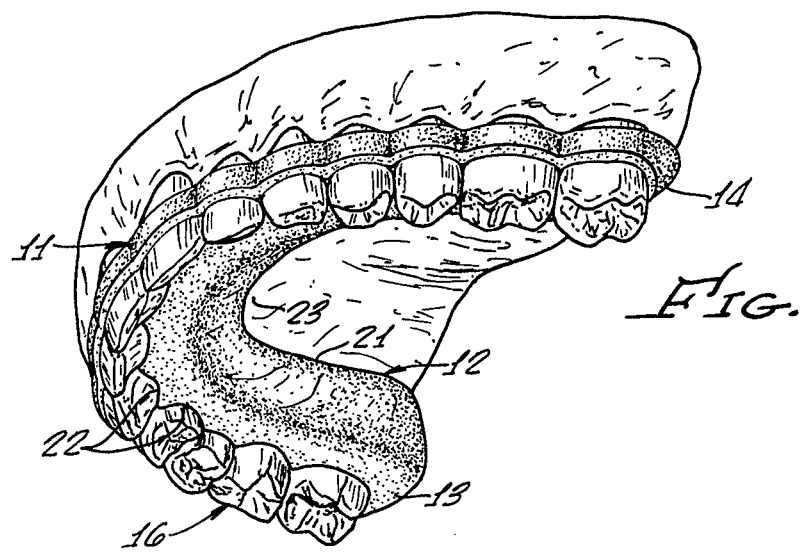
FIG. 2.
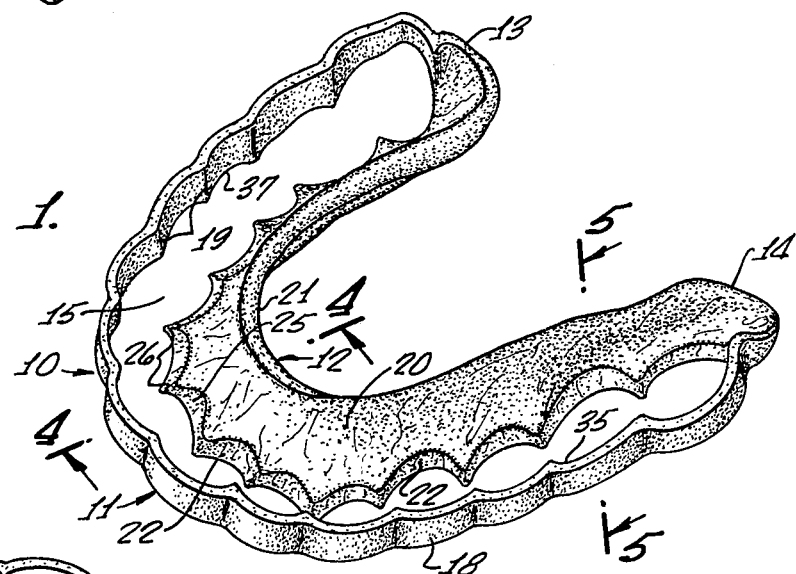
FIG. 1.
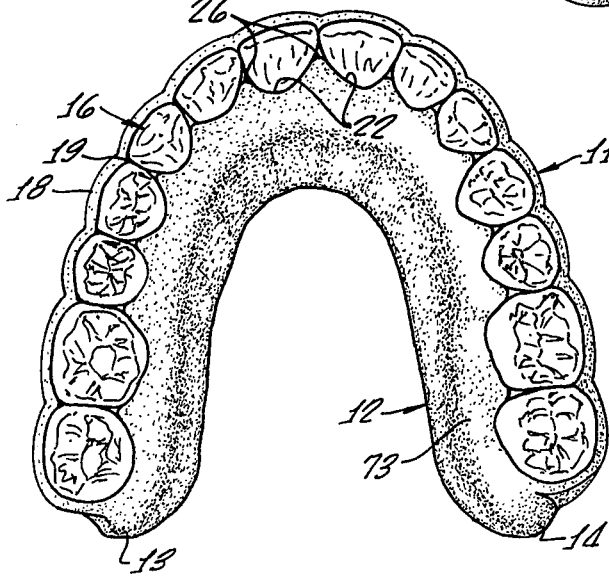
FIG. 3.
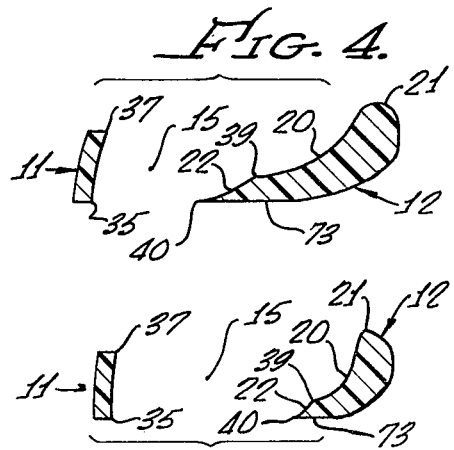
FIG. 4.
FIG. 5.

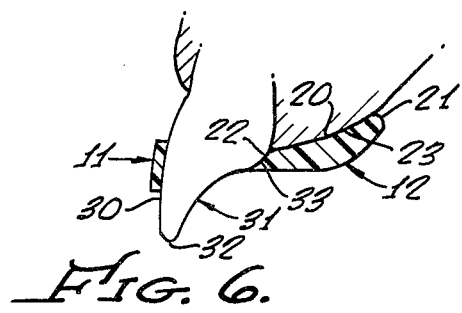
FIG. 6.
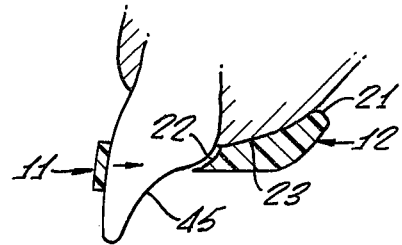
FIG. 10.
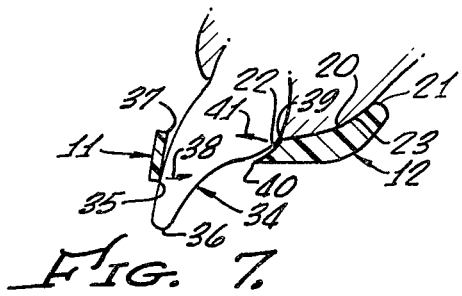
FIG. 7.
FIG. 11.
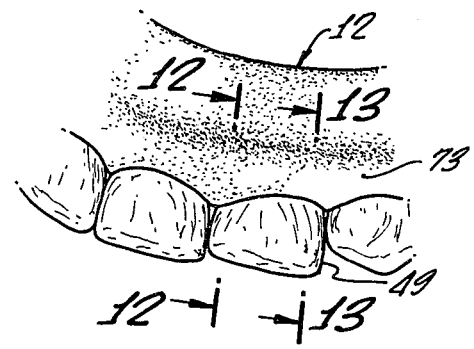
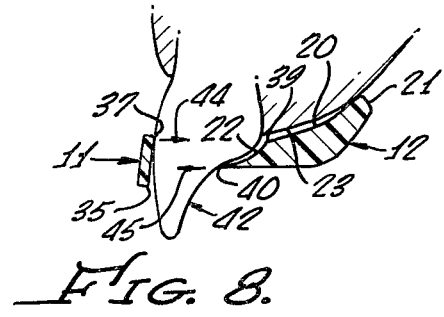
FIG. 8.
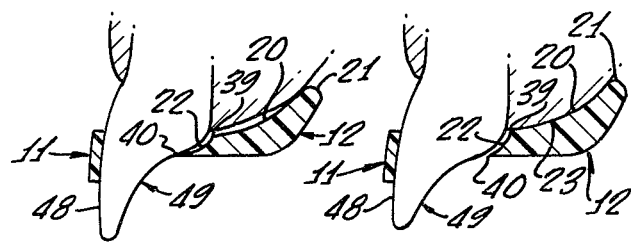
FIG. 13.  FIG. 12.
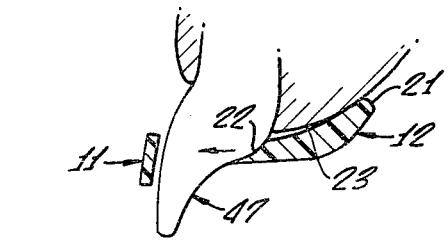
FIG. 9.
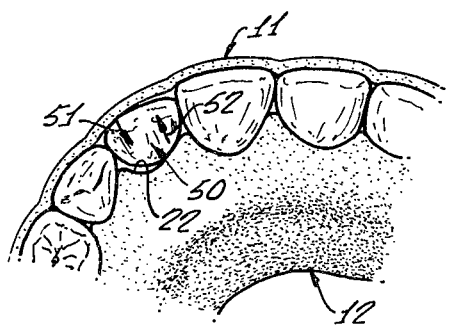
FIG. 14.

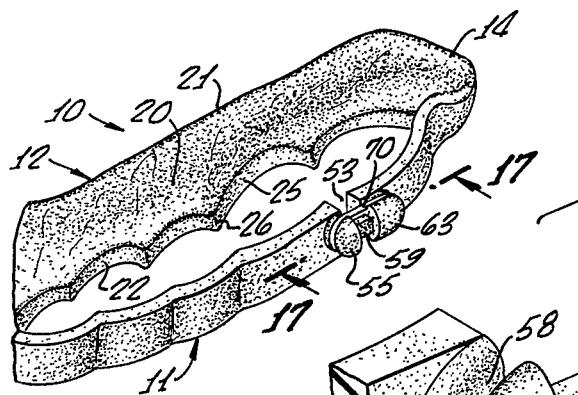
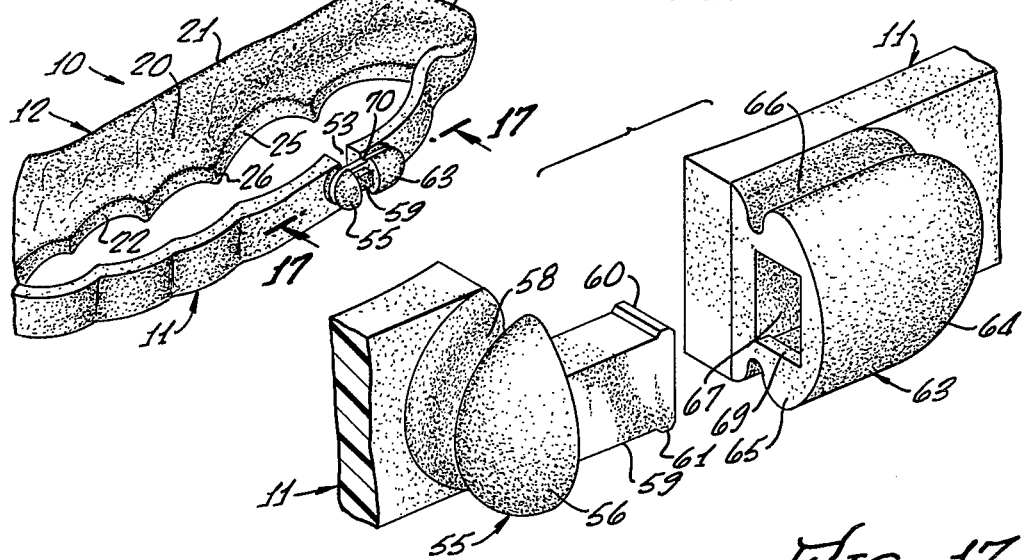
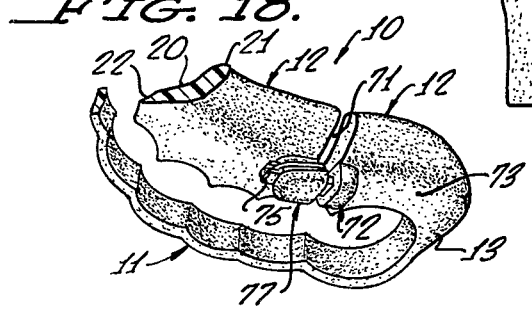
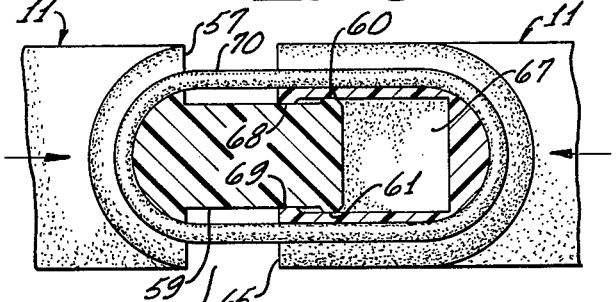
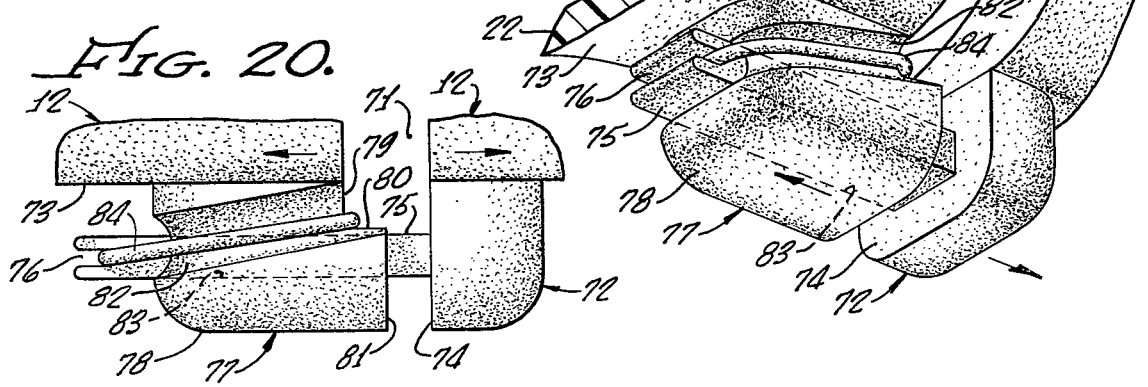

ORTHODONTIC APPLIANCE

In orthodontics, after major tooth movements have been effected by braces, it is necessary to retain the teeth in their new positions for a period of time and frequently to accomplish minor tooth movements to complete the teeth straightening operation. Customarily, a retainer plate is used, fitting on the roof of the mouth with wires for extending around the teeth to hold or move them. This has several disadvantages. The wires are difficult to bend accurately, and are susceptible to breakage. The plate to which the wires are attached is uncomfortable to wear and must be removed and cleaned regularly. It may affect the speech because of extending across the roof of the mouth. Moreover, the wires are unsightly and so detract from the appearance of the person wearing the device.

Alternative devices have been proposed, but have had only limited utility. The appliances shown in U.S. Pat. Nos. 2,467,432, 2,479,780 and 4,073,061 fit between the occlusal surfaces of the upper and lower teeth, having recesses for receiving the teeth to retain them. Obviously, this type of appliance cannot be worn all the time because it does not allow for movement of the jaws. These devices are bulky, cumbersome and may cause patient discomfort.

In U.S. Pat. No. 646,629, an elastic plate is proposed which has inner and outer portions overlying the facial and lingual surfaces of the teeth. These inner and outer portions are connected by end segments which extend over the crowns of the teeth so that the appliance prevents occlusion of the upper and lower teeth. Moreover, the appliance of this patent can produce only limited types of tooth movement and cannot perform such operations as torquing the teeth or tipping them.

Consequently, there has remained an acute need for an orthodontic appliance which will effectively retain the teeth which can be used selectively to accomplish predetermined tooth movements.

The present invention provides an orthodontic appliance which is shaped to the general contour of the teeth and the adjacent gingiva in compliance with the patient's arch form. It is a generally U-shaped device with spaced inner and outer portions that define an opening which receives an entire row of teeth. The crowns of the teeth extend through the opening so that their occlusal surfaces of the teeth are left entirely exposed. The inner and outer portions can be made to selectively engage portions of the teeth to accomplish either retention or tooth movement. Many kinds of tooth movement can be achieved so the device has broad applicability. Only a narrow, thin band is exposed on the facial side of the teeth, which is unobtrusive. It may be made of transparent material or colored to match the color of the teeth so that it is all but invisible. The appliance is small, light weight, and is very comfortable. It does not extend over the roof of the mouth so that the action of the tongue in speaking is not affected. The appliance is easily snapped into position over the row of teeth, can be left in place for long periods of time, does not interfere with eating, and yet is easily removed. Tooth movements can be accomplished in greater degree than with appliances of the prior art. This, in turn, allows the bands to be removed earlier because of the increased movement that can be accomplished by the appliance.

BRIEF DESCRIPTION OF THE DRAWINGS

FIG. 1 is a perspective view of the orthodontic appliance of this invention;

FIG. 2 is a perspective view of the appliance as associated with a row of teeth;

FIG. 3 is a plan view of the appliance as associated with a row of teeth;

FIG. 4 is a transverse sectional view, taken along line 4—4 of FIG. 1;

FIG. 5 is a transverse sectional view, taken along line 5—5 of FIG. 1;

FIG. 6 is a fragmentary sectional view of the appliance as used in retaining a tooth;

FIG. 7 is a fragmentary sectional view of the appliance as used in torquing a tooth inwardly;

FIG. 8 is a fragmentary sectional view illustrating the appliance as used in torquing a tooth outwardly;

FIG. 9 is a fragmentary sectional view illustrating the appliance as used in displacing a tooth outwardly;

FIG. 10 is a fragmentary sectional view of the appliance as used in displacing a tooth inwardly;

FIG. 11 is a fragmentary perspective view of the appliance as used for tipping a tooth;

FIG. 12 is a transverse sectional view, taken along line 12—12 of FIG. 11;

FIG. 13 is a transverse sectional view, taken along line 13—13 of FIG. 11.

FIG. 14 is a plan view illustrating the use of the appliance in rotating a tooth.

FIG. 15 is a fragmentary perspective view of the appliance as modified for causing the outer portion to exert a greater posterior force;

FIG. 16 is an enlarged fragmentary exploded perspective view of various components of the arrangement of FIG. 15.

FIG. 17 is an enlarged fragmentary sectional view, taken along line 17—17 of FIG. 15.

FIG. 18 is a fragmentary perspective view of the appliance as arranged to provide increased anterior force of the inner portion of the appliance.

FIG. 19 is an enlarged fragmentary perspective view of the operative components of the arrangement of FIG. 18; and FIG. 20 is an enlarged fragmentary side elevational view of the operative components of the arrangement of FIG. 18.

DETAILED DESCRIPTION OF THE PREFERRED EMBODIMENT

The orthodontic appliance 10 of this invention, as seen in FIGS. 1, 2 and 3, is an integral, one piece element, preferably made of plastic, having a degree of flexibility but which is inelastic. The appliance 10 is of generally U-shaped contour in compliance with the arch form of the patient making use of the appliance. The appliance is made up of an outer or facial band 11 and a lingual or inside section 12, which are joined together by interconnecting portions 13 and 14 at the ends of the appliance. The sections 11 and 12 are spaced apart so as to leave an opening 15 between them which receives the entire row 16 of the patient's teeth when the appliance is installed as seen in FIGS. 2 and 3. In the installed position, the interconnecting segments 13 and 14 extend around the distal surfaces of the posterior teeth at the ends of the row. This leaves the occlusal surfaces of the teeth unobstructed.

The outer segment 11 of the appliance resembles a ribbon of material with its principal surfaces generally vertical, as illustrated. The inner surfaces of this portion of the appliance is made generally complementary to the facial surfaces of the teeth in the row 16, although its width is considerably less than the height of the teeth. This contouring produces a series of curved portions 18 that meet at their ends so as to produce spaced substantially vertical ribs 19. The latter elements extend part way into the spaces between the teeth and may engage the mesial and distal surfaces of adjacent teeth as the curved portions 18 overlie the facial tooth surfaces. To avoid discomfort of the patient, the section 11 preferably does not exceed four millimeters in thickness.

The inner section 12 of the appliance includes a concave portion 20 that extends downwardly, as illustrated in FIG. 1, from an inner edge 21 and terminates at a beveled edge 22 at the opening 15. The concave portion 20 is complementary to the gingiva 23 adjacent the teeth and the edge 22 is made generally complementary to the lingual surfaces of the teeth at their cervixes. The edge 22, by being generally complementary to the tooth surfaces, includes a series of curved portions 25 which meet at points 26. This enables the edge 22 to engage the lingual tooth surfaces while the points 26 fit between adjacent teeth and may engage their mesial and distal surfaces. Only the edge 22 engages the teeth so the area of contact is relatively small and at the cervixes, well below the occlusal surfaces.

The inner section 12 is wider than the outer section 11 and may be slightly thicker which causes it to have much less flexibility than that of the outer section 11. The relative rigidity of the inner portion is utilized in cooperation with the flexibility of the outer portion in accomplishing various tooth movements, as explained below. The rigidity of the inner section 12 is enhanced by its contour by which the concave section 20 curves toward a horizontal plane, as the appliance is shown, adjacent to the beveled edge 22. The central portion of the inner section 12 has a more shallow inclination than do the two end portions, as may be seen in FIGS. 4 and 5.

The appliance 10 is produced by first making a plaster model of the patient's teeth. If certain teeth of the patient are to be repositioned, the corresponding teeth of the model are relocated to the desired positions. Then plastic material is positioned over the model and subjected to heat and pressure. This causes the plastic material to assume precisely the contour of the model, thereby corresponding to the contour of the patient's mouth with a desired final orientation of the teeth. The molded plastic then is trimmed to the shape shown in FIG. 1, removing excess material and producing the opening 15. The trimming of the appliance may be done selectively so as to provide different types of tooth movement as explained below. It may be devised to retain the positions of some of the teeth with which it is associated, while accomplishing various kinds of movements of the other teeth.

When the appliance 10 is used to retain a tooth without causing movement, it engages the tooth as shown in FIG. 6. The outer section 11 of the appliance complementarily overlies the facial surface 30 of the tooth 31 below the occlusal surface 32. The edge 22 of the inner section 12 similarly engages the cervical portion 33 of the tooth 31 on the lingual side. The concave portion 20 of the inner section 12 complementarily engages the tissue 23 of the patient's mouth adjacent the lingual surface of the tooth 31. The inner section 12 is of limited width, so that the roof of the patient's mouth is unobstructed by the appliance.

In FIG. 7, the appliance 10 is shown as used in torquing a protruding tooth inwardly. Because the tooth 34 of FIG. 7 is inclined outwardly, and the free position of the outer section 11 corresponds to a desired position of the tooth which is more nearly vertical, the engagement by the outer section 11 will be only along its lower corner 35, i.e., the corner adjacent the occlusal surface 36 of the tooth. The remainder of the portion 11 to its opposite corner 37 is spaced from the facial surface of the tooth. As a result, the outer section 11 of the appliance produces a force on the tooth as indicated by the vector 38.

On the inside, the outwardly inclined tooth 24 is engaged by the edge surface 22 only at a location adjacent its corner 39 where the edge surface 22 joins the concave surface 20. At other locations, including the outer corner 40, the edge surface 22 is spaced from the lingual surface of the tooth. Consequently, the inner section 12 produces a reaction on the tooth as represented by the vector 41, which is closer to the cervix of the tooth than is the vector 28. As a result, the force vectors 38 and 41 produce a counterclockwise moment, as illustrated. After the appliance has been maintained on the teeth for an adequate period of time, the tooth 34 will be torqued inwardly to a predetermined position of proper alignment. When the predetermined location of the tooth is reached, the outer portion 11 and the edge surface 22 will complementarily engage the tooth surfaces, and the tooth will be retained without further movement.

The appliance also may be used to torque a tooth outwardly in the manner shown in FIG. 8. For such a tooth 42, the outer section 11 engages the tooth only at its upper corner 37 (the corner adjacent the cervix of the tooth), being spaced otherwise from the facial surface of the tooth. On the inside, the engagement by the section 12 is only at the outer corner 40 of the beveled edge surface 22, which is closer to the occlusal surface 43 of the tooth than is the opposite corner 39. If necessary, the edge surface 22 may be made slightly elongated to cause its outer corner 40 to engage the lingual surface of the tooth, and the remainder of the surface 22 to be spaced from the tooth. When the tooth is engaged in this manner, the concave surface 20 of the inner section 12 also may be spaced slightly from the tissue 23 of the mouth, except at the inner edge 21 of the section 12.

The outer section 11, at its corner 37, engages the tooth at a location further from the cervix of the tooth 42 than that of the inner section 12 at the corner 40. As a result, the reaction provided by the outer section 11, represented by the vector 44, couples with the reaction from the inner section 12, as indicated by the vector 45, to produce a clockwise moment on the tooth 40 as it is shown in FIG. 8. Consequently, over a period of time, the tooth is caused to rotate outwardly to the desired position, where it is retained.

When a tooth simply is to be displaced outwardly without rotation, it is engaged as shown in FIG. 9. Here, the outer section 11 is spaced entirely away from the facial surface of the tooth 46. On the inside, however, the surface 22 of the section 12 engages the lingual surface of the tooth complementarily. This produces an unopposed outward reaction that in time displaces the tooth outwardly until its facial surface meets the outer section 11 of the appliance. The concave surface 20 of the inner section 12 may be spaced slightly above the tissue 23 of the mouth as shown in FIG. 9 until the desired tooth movement has occurred. When the tooth 46 reaches the outer section 11, it is retained against further movement.

In FIG. 10, the appliance 10 is arranged to displace a tooth inwardly. Here, the outer section 11 complementarily engages the tooth 47, thereby producing an inwardly directed force. The edge surface 22, however, is spaced away from the lingual surface of the tooth. Consequently, the force produced by the outer section 11 is unopposed and the tooth is caused to be moved inwardly as the appliance is worn. This movement continues until the lingual surface of the tooth is brought into engagement with the edge surface 22 of the inner section 12 after which the tooth is retained.

Tipping of the tooth may be accomplished in the manner shown in FIGS. 11 through 13. Here, the outer section 11 of the appliance complementarily engages the facial surface 48 of the tooth 49 to retain it against outward movement. On the inside, the edge surface 22 is shaped so as to engage the lingual surface of the tooth only at the side which is to be shifted gingivally, while being spaced from it at the location where the tooth is to be permitted to move occlusally. Thus, the surface 22 adjacent the high side of the tooth, as seen in FIG. 12, engages the lingual tooth surface. At the opposite side of the tooth, however, where occlusal movement is to be allowed, the surface 22 is spaced from the lingual surface of the tooth. This spacing is maintained because of the relative rigidity of the inner section 12 of the appliance. There is produced, therefore, a force toward the gingiva on the high side of the tooth, a reaction that tips the tooth ultimately to its proper orientation.

Rotation of the tooth is shown in FIG. 14. Here it is necessary to rotate the tooth 50 in a counterclockwise direction, as the tooth is illustrated. To accomplish this, the outer section 11 engages the facial surface of the tooth only at the distal or left-hand portion of the tooth as it is shown. At the mesial side, the section 11 is spaced away from the tooth. The result is an inward force, represented by the vector 51, at the distal portion of the tooth.

On the inside, the surface 22 is shaped so that it engages the lingual surface of the tooth only at its mesial portion. At the distal portion, the surface 22 is spaced from the tooth. Consequently, the inner portion 12 produces an outward reaction represented by the vector 52 at the lingual side of the mesial portion of the tooth. The forces represented by vectors 51 and 52 produce a couple which rotates the tooth counterclockwise, as illustrated, until its proper rotational position is reached and its facial and lingual surfaces complementarily engage the portions 11 and the surface 22 of the portion 12 of the appliance.

From the foregoing, it can be seen that the appliance of this invention has broad applicability, being capable of producing many kinds of tooth movement. This can be accomplished selectively in a single appliance so that the teeth may be moved to suit their individual requirements or simply retained in position as needed.

For greater amounts of tooth movement, the appliance may be modified to provide a positive posterior force by the outer section 11, or a positive anterior force by the inner section 12.

As illustrated in FIGS. 15, 16 and 17, the outer section 11 is split at its end portion adjacent to the interconnecting segment 14. In most instances, an identical provision is made on the opposite side of the outer section 11, only one side being illustrated for simplicity. Secured to the outer surface of the section 11 on the forward or anterior side of the gap 53 is a small post 55, having a rounded mesial surface 56 and a flat distal surface 57. A groove 58 is formed in the mesial surface 56. Projecting horizontally from a distal surface 57, in the same general direction as the section 11, is a tongue 59 which is of constant lateral dimension except for small flanges 60 and 61 at the top and bottom of its outer end.

On the rearward or posterior side of the gap 53 in section 11 is an additional post 63 of greater horizontal dimension, having a rounded outer surface 64 and a flat mesial surface 65. A groove 66 is formed in rounded outer surface 64. A rectangular opening 67 is formed in the post 63, extending inwardly from its mesial surface 65. The opening 67 is of constant lateral dimension, except for its entrance which is slightly restricted by opposed flanges 68 and 69.

The posts 55 and 63 are assembled by snapping the tongue 50 through the restricted entrance into the opening 67 of the post 63. This prevents withdrawal of tongue 59 from the opening 67. The tongue 59 cooperates with the wall of the opening 67 to guide the two segments of the outer portion 11, keeping them in alignment. In order to apply a force on the section 11, an elastic band 70 is extended around the posts 55 and 63 at their grooves 58 and 66 which retain the band. The result is a force tending to pull the two segments of the section 11 together, thereby causing the section 11 to exert an increased posterior force on the surfaces of the teeth which it engages. This reaction is absorbed through the relatively rigid inner section 12. Maximum tooth movement is limited by interengagement of the adjacent surfaces 57 and 65 of the posts 55 and 63.

For anterior movement of the inner section 12, it is severed adjacent its outer ends as indicated in FIGS. 18, 19 and 20. Here, only one side of the appliance is illustrated, the arrangement at the opposite side usually being identical. The section 12 is severed so as to leave a gap 71 at its rearward portion adjacent the interconnecting segment 13. On the distal side of the gap 71, a post 72 is attached to the outer surface 73 of the inner section 12. This post has a rounded outer contour with a flat mesial surface 74. A tongue 75 projects from the surface 74, extending generally parallel to the surface 73. A transverse slot 76 is formed in the outer end of the tongue 75. On the mesial side of the gap 72, a second post 77 is attached, again being given a rounded outer surface 78. Post 77 has a flat inner distal surface 79, a short surface 80 at right angles to the surface 79, and generally parallel to the surface 79. A groove 82 is formed in the post 77, extending around the outer surface of the post to the surfaces 79 and 80. An opening 83 extends through the post 77 generally parallel to the surface 73 from the distal surface 81 to the opposite end of the post at the groove 82. The opening 83 is rectangular in cross section and complementary to the tongue 75.

In use of the force-producing arrangement for the section 12, the tongue 75 is extended through the post 77 at the opening 83. This guides the two segments of the section 12 so that alignment is maintained. An elastic band 84 fits around the post 77, being retained by the surfaces 79 and 80, and extending through the side portions of the groove 82. The elastic band 84 also is received within the slot 76 of the tongue 75 where the walls of the slot retain it. Consequently, the elastic band 84 produces a reaction biasing the tongue 75 to the right, as illustrated in FIGS. 19 and 20, and the post 77 to the left as shown in those views. Therefore, the two segments of the section 12 at the gap 71 are urged apart so that the section 12 then produces an anterior force on the teeth that it engages. By being relatively rigid, the inner section 12 can withstand the compressive force applied to it in this manner. The total movement permitted the section 12 in moving the teeth anteriorly is limited by interengagement of the forward surface 74 of the post 73 and the distal surface 81 of the post 77.

Although illustrated and described in association with upper teeth, the appliance of this invention is applicable equally to lower teeth.

The foregoing detailed description is to be clearly understood as given by way of illustration and example only, the spirit and scope of this invention being limited solely by the appended claims.

We claim:

1. An orthodontic appliance comprising:
    a generally U-shaped member, having
        an outer portion having its principal surface substantially vertical, and contoured so as to be generally complementary to and adapted to engage portions of the facial surfaces of at least some of the teeth with such engagement being only intermediate the occlusal surfaces and the gingiva of a row of teeth, an inner portion spaced from said outer, portion, and
        connecting portions interconnecting the ends of said inner and outer portions so that said member defines an opening dimensioned to receive all of the teeth of such a row of teeth so that the teeth extend through said opening with the occlusal areas exposed with said connecting portions extending around the distal surfaces of the posterior teeth of such a row of teeth,
        said inner portion having a first surface contoured to be generally complementary to and adapted to engage portions of the lingual surfaces adjacent the gingiva and remote from the occlusal surfaces of at least some of the teeth of such a row of teeth, and a concave surface inwardly of said edge surface and adapted to generally complementarily engage the gingiva adjacent said lingual surfaces of said teeth, whereby said inner and outer portions cooperate to selectively move or retain said teeth.

2. A device as recited in claim 1 in which said first surface of said inner portion is defined by an edge of said inner portion,
    at least a part of said edge being beveled, and said concave surface is a principal surface of said inner portion connected to said edge.

3. A device as recited in claim 2 in which said outer portion is a relatively thin band having a series of arcuate portions interconnected at rib-like segments adapted to extend into spaces between the teeth on the facial side of a row of teeth.

4. A device as recited in claim 3 in which said edge of said inner portion has a series of arcuate portions interconnected by points adapted to extend into the spaces between the teeth on the lingual side of a row of teeth.

5. A device as recited in claim 1 in which said outer portion is flexible and said inner portion is less flexible than said outer portion.

6. A device as recited in claim 5 in which said inner portion has a greater thickness than does the outer portion.

7. A device as recited in claim 4 in which said outer portion has a thickness no greater than four millimeters.

8. A device as recited in claim 1 including means for exerting a force for biasing said outer portion posteriorly.

9. A device as recited in claim 8 in which said outer portion includes a split, and in which said means for exerting a force for biasing said outer portion posteriorly includes a resilient means at said split.

10. A device as recited in claim 8 in which said outer portion includes a split and said means for biasing said outer portion posteriorly includes
    a first element projecting outwardly from said outer portion on the mesial side of said split,
    a second element projecting outwardly from said outer portion on the distal side of said split,
    an elastic band extending around said first and second elements for biasing said first and second elements toward each other for thereby biasing said outer portion posteriorly, and guide means for retaining said first and second elements in predetermined alignment at said split.

11. A device as recited in claim 10 in which said guide means includes a tongue projecting from one of said elements, the other of said elements defining an opening receiving said tongue.

12. A device as recited in claim 11 in which each of said first and second elements includes a groove in the outer surface thereof, said elastic band being received in said groove for thereby retaining said elastic band to said first and second elements.

13. A device as recited in claim 8 in which said outer portion is split in two places,
    each of said places being adjacent one
    of said interconnecting portions, and said means for exerting a force for biasing said outer portion posteriorly includes a resilient member at either of said places biasing the split portions of said outer portion toward each other.

14. A device as recited in claim 1 including means for exerting a force for biasing said inner portion anteriorly.

15. A device as recited in claim 14 in which said inner portion includes a split and said means for exerting a force for biasing said inner portion anteriorly includes a resilient means in said split.

16. A device as recited in claim 14 in which said inner portion includes a split, and said means for biasing said inner portion anteriorly includes
    a first element connected to said inner portion on the mesial side of said split,
    a second element connected to said inner portion on the distal side of said split,
    and an elastic band engaging said first and second elements for biasing said first and second elements apart, for thereby biasing said inner portion anteriorly.

17. A device as recited in claim 16 in which
    said second element includes a tongue projecting outwardly therefrom,
    said first element includes an opening therethrough,
        said tongue extending through said opening and having an outer end portion outwardly of said first element on the mesial side thereof,
    said elastic band extending around said first element and engaging said outer end portion of said tongue.

18. A device as recited in claim 17 in which said outer end portion of said tongue is slotted, said elastic band being received in said slot.

19. A device as recited in claim 18 including means for retaining said elastic band to said first element.

20. A device as recited in claim 9 in which said inner portion is split in two places,
   each of said places being adjacent one
      of said interconnecting portions, and said means for exerting a force for biasing said inner portion anteriorly includes a resilient member at either of said two places biasing the split portions of said outer portion apart.

21. The method of retaining the position of a tooth of a row of teeth comprising the steps of
   preparing a flexible substantially inelastic generally U-shaped member,
   forming an opening in said member so as to provide an outer portion, an inner portion and a connecting portion interconnecting said outer and inner portions at either end of said member, associating said member with said row of teeth such that said outer portion is adjacent the facial surfaces of said teeth, said inner portion is adjacent the lingual surfaces of said teeth, and overlies the gingiva adjacent said lingual surfaces, said connecting portions extend around the distal surfaces of the posterior ones of said teeth, and the crowns of said teeth extend through said opening,
   and complementarily engaging facial portions of said tooth by said outer portion and lingual portions of said tooth by said inner portion, thereby to hold said tooth substantially in said position.

22. The method of torquing inwardly an outwardly inclined tooth of a row of teeth comprising the steps of preparing a flexible substantially inelastic generally U-shaped member,
   forming an opening in said member so as to provide an outer portion, an inner portion and a connecting portion interconnecting said outer and inner portions at either end of said member,
   associating said member with said row of teeth such that said outer portion is adjacent the facial surfaces of said teeth, said inner portion is adjacent the lingual surfaces of said teeth, and overlies the gingiva adjacent said lingual surfaces, said connecting portions extend around the distal surfaces of the posterior ones of said teeth, and the crowns of said teeth extend through said opening, engaging the facial surface of said tooth with said outer portion so as to produce an inward reactive force on said tooth,
   and simultaneously engaging the lingual surface of said tooth with said inner portion so as to produce an outward reactive force on said tooth,
      with said inner portion engaging said tooth relatively closer to the cervix thereof than does said outer portion, whereby said outer and inner portions produce a force couple rotationally biasing said tooth inwardly,
   and maintaining said tooth so engaged for a time sufficient to cause said tooth to be rotated into substantially complementary engagement with said inner and outer portions.

23. The method of torquing outwardly an inwardly inclined tooth of a row of teeth comprising the steps of preparing a flexible substantially inelastic generally U-shaped member,
   forming an opening in said member so as to provide an outer portion, an inner portion and a connecting portion interconnecting said outer and inner portions at either end of said member,
   associating said member with said row of teeth such that said outer portion is adjacent the facial surfaces of said teeth, said inner portion is adjacent the lingual surfaces of said teeth, and overlies the gingiva adjacent said lingual surfaces, said connecting portions extend around the distal surfaces of the posterior ones of said teeth, and the crowns of said teeth extend through said opening,
   engaging the facial surface of said tooth with said outer portion so as to produce an inward reactive force on said tooth,
   and simultaneously engaging the lingual surface of said tooth with said inner portion so as to produce an outward reactive force on said tooth,
      with said outer portion engaging said tooth relatively closer to the cervix thereof than does said inner portion, whereby said outer and inner portions produce a force couple rotationally biasing said tooth outwardly,
   and maintaining said tooth so engaged for a time sufficient to cause said tooth to be rotated into substantially complementary engagement with said inner and outer portions.

24. The method of displacing inwardly a tooth of a row of teeth comprising the steps of preparing a flexible substantially inelastic generally U-shaped member,
   forming an opening in said member so as to provide an outer portion, an inner portion and a connecting portion interconnecting said outer and inner portions at either end of said member,
   associating said member with said row of teeth such that said outer portion is adjacent the facial surfaces of said teeth, said inner portion is adjacent the lingual surfaces of said teeth, and overlies the gingiva adjacent said lingual surfaces, said connecting portions extend around the distal surfaces of the posterior ones of said teeth, and the crowns of said teeth extend through said opening,
   and substantially complementarily engaging the facial surface of said tooth with said outer portion so as to produce an inward reactive force on said tooth while maintaining said inner portion spaced a predetermined distance from the lingual surface of said tooth, and maintaining said tooth so engaged for a time sufficient to cause said tooth to be shifted inwardly into substantial engagement with said inner portion in response to said force.

25. The method of displacing outwardly a tooth of a row of teeth comprising the steps of preparing a flexible substantially inelastic generally U-shaped member,
   forming an opening in said member so as to provide an outer portion, an inner portion and a connecting portion interconnecting said outer and inner portions at either end of said member,
   associating said member with said row of teeth such that said outer portion is adjacent the facial surfaces of said teeth, said inner portion is adjacent the lingual surfaces of said teeth, and overlies the gingiva adjacent said lingual surfaces, said connecting portions extend around the distal surfaces of the posterior ones of said teeth, and the crowns of said teeth extend through said opening,
   and substantially complementarily engaging said lingual surface of said tooth with said inner portion so as to produce an outward reactive force while maintaining said outer portion spaced a predetermined distance from the facial surface of said tooth, and maintaining said tooth so engaged for a time sufficient to cause said tooth to be shifted outwardly into substantial engagement with said outer portion in response to said force.

26. The method of tipping a misaligned tooth having one side spaced farther from the gingiva than the other comprising the steps of preparing a flexible substantially inelastic generally U-shaped member, forming an opening in said member so as to provide an outer portion, an inner portion and a connecting portion interconnecting said outer and inner portions at either end of said member, associating said member with said row of teeth such that said outer portion is adjacent the facial surfaces of said teeth, said inner portion is adjacent the lingual surfaces of said teeth, and overlies the gingiva adjacent said lingual surfaces, said connecting portions extend around the distal surfaces of the posterior ones of said teeth, and the crowns of said teeth extend through said opening, engaging the lingual portion of said tooth on said one side thereof with said inner portion so as to produce a reaction toward the gingiva while maintaining other lingual portions of said tooth spaced from said inner portion, and maintaining said tooth so engaged until said force has tipped said tooth to a predetermined position.

27. The method of rotationally aligning a tooth of a row of teeth which tooth is rotationally misaligned by having a facial portion outwardly of a desired location and a lingual portion inwardly of a desired location comprising the steps of preparing a flexible substantially inelastic generally U-shaped member, forming an opening in said member so as to provide an outer portion, an inner portion and a connecting portion interconneccting said outer and inner portions at either end of said member, associating said member with said row of teeth such that said outer portion is adjacent the facial surfaces of said teeth, said inner portion is adjacent the lingual surfaces of said teeth, and overlies the gingiva adjacent said lingual surfaces, said connecting portions extend around the distal surfaces of the posterior ones of said teeth, and the crowns of said teeth extend through said opening, and substantially complementarily engaging said facial portion of said tooth with said outer portion of said member while maintaining other facial portions of said tooth spaced a predetermined distance from said outer portion of said member, simultaneously engaging said lingual portion of said tooth with said inner portion of same member while maintaining other lingual portions of said tooth spaced a predetermined distance from said inner portion of said member, whereby said inner and outer portions of said member produce a force couple rotationally biasing said tooth toward a position of rotational alignment, and maintaining said tooth as engaged until said tooth is rotated such that said other facial portions of said tooth are brought substantially into engagement with said outer portion of said member and said other lingual portions of said tooth are brought substantially into engagement with said inner portion of said member.

* * * * *